US011311404B2

(12) United States Patent
Aravalli

(10) Patent No.: US 11,311,404 B2
(45) Date of Patent: Apr. 26, 2022

(54) STOMAL DIVERTER DEVICE

(71) Applicant: Covidien LP, Mansfield, MA (US)

(72) Inventor: AVVLN Srinivasa Murthy Aravalli, Hyderabad (IN)

(73) Assignee: Covidien LP, Mansfield, MA (US)

( * ) Notice: Subject to any disclaimer, the term of this patent is extended or adjusted under 35 U.S.C. 154(b) by 783 days.

(21) Appl. No.: 16/160,226

(22) Filed: Oct. 15, 2018

(65) Prior Publication Data

US 2019/0201230 A1     Jul. 4, 2019

Related U.S. Application Data

(60) Provisional application No. 62/613,433, filed on Jan. 4, 2018.

(51) Int. Cl.
    *A61F 5/44*            (2006.01)
    *A61F 5/449*          (2006.01)
    (Continued)

(52) U.S. Cl.
    CPC .............. *A61F 5/4407* (2013.01); *A61B 1/05* (2013.01); *A61F 5/443* (2013.01); *A61F 5/445* (2013.01);
    (Continued)

(58) Field of Classification Search
    CPC ...... A61F 5/4407; A61F 5/4405; A61F 5/443; A61F 5/449; A61F 5/445; A61F 2005/4455; A61F 5/44; A61F 5/4404; A61B 17/11; A61B 2017/1103; A61B 2017/1125; A61B 17/1114; A61B 2017/1117; A61B 2017/1121; A61B 17/12022;
    (Continued)

(56) References Cited

U.S. PATENT DOCUMENTS 3,483,868 A * 12/1969 Marsan .................... A61F 5/445
                                                    604/339
3,937,224 A * 2/1976 Uecker .................... A61F 5/445
                                                  604/101.05

(Continued)

FOREIGN PATENT DOCUMENTS

EP           2027835 A1     2/2009
WO         9943277 A1     9/1999

(Continued)

OTHER PUBLICATIONS

European Search Report dated Jun. 25, 2019, issued in EP Appln. No. 19150146.

(Continued)

*Primary Examiner* — Nicholas J. Weiss
*Assistant Examiner* — Alessandro R Del Priore

(57) ABSTRACT

A stomal diverter device includes a catheter, a stoma rod, and a bracket. The catheter includes a first tube having an open end, a second tube spaced from the first tube having a closed end, and a drain tube. The stoma rod is positioned between the first and second tubes and includes structure to releasably attach the stoma rod to the abdomen of the patient. The bracket is supported on the catheter and the stoma rod and defines a locking feature that is configured to engage a mating feature of the stoma rod to secure the catheter between the stoma rod and the bracket.

17 Claims, 6 Drawing Sheets

(51) Int. Cl.
*A61F 5/445* (2006.01)
*A61B 1/05* (2006.01)
*A61F 5/443* (2006.01)

(52) U.S. Cl.
CPC ............ *A61F 5/4405* (2013.01); *A61F 5/449* (2013.01); *A61F 2005/4455* (2013.01)

(58) Field of Classification Search
CPC ........ A61B 17/12027; A61B 17/12031; A61B 17/12036; A61B 17/1204; A61B 17/12045
See application file for complete search history.

(56) References Cited

U.S. PATENT DOCUMENTS

| | | | | |
|---|---|---|---|---|
| 4,671,272 | A | * | 6/1987 | Steer ..................... A61B 90/00 606/1 |
| 5,026,361 | A | * | 6/1991 | Matysiak ................ A61F 5/445 604/338 |
| D783,814 | S | | 4/2017 | Hanuka et al. |
| 2003/0163121 | A1 | * | 8/2003 | Leiboff .................. A61B 90/00 606/1 |
| 2008/0004580 | A1 | | 1/2008 | Mullejans et al. |
| 2008/0097491 | A1 | * | 4/2008 | Gobel ................. A61B 17/0644 606/153 |
| 2008/0228132 | A1 | * | 9/2008 | Langenbach ..... A61M 39/0208 604/30 |
| 2013/0197458 | A1 | * | 8/2013 | Salama ................. A61F 5/4405 604/335 |
| 2015/0057626 | A1 | | 2/2015 | Hanuka et al. |
| 2015/0367111 | A1 | * | 12/2015 | Kane ................... A61J 15/0049 604/9 |

FOREIGN PATENT DOCUMENTS

| | | |
|---|---|---|
| WO | 2011007355 A2 | 1/2011 |
| WO | 2014181338 A2 | 11/2014 |

OTHER PUBLICATIONS

European Office Action dated Jul. 15, 2020, issued in EP Appln. No. 19 150 146, 4 pages.

* cited by examiner

STOMAL DIVERTER DEVICE

CROSS-REFERENCE TO RELATED APPLICATION

This application claims the benefit of and priority to U.S. Provisional Patent Application No. 62/613,433 filed Jan. 4, 2018, the entire disclosure of which is incorporated by reference herein.

BACKGROUND

1. Technical Description

The present disclosure is directed to a device and method for performing an ostomy procedure and, more particularly, to a stomal diverter device and method of using the stomal diverter device during an ostomy procedure.

2. Background of Related Art

During an ostomy procedure, a portion of an internal body vessel, such as the intestine or colon, is exteriorized to form a stoma. Stomas may be created in conjunction with an ostomy procedure by securing a bisected portion of the internal body vessel to the abdominal wall to provide internal access into the internal body vessel for collecting fecal matter. Ostomy surgery is sometimes performed on an emergency basis due to diverticulitis, trauma, radiation complications, volvulus, necrotic bowel, bowel perforation, etc. An ostomy may be temporary to allow for healing of the bowel or a decrease of inflammation at a surgical site. In some instances, an ostomy may be permanent.

In ostomy procedures, the internal body vessel is secured to the abdominal wall and/or cutaneous tissue of the abdomen. Securing the internal body vessel to the abdominal wall and/or the cutaneous tissue of the abdomen keeps the stoma in the desired location and prevents it from withdrawing back into the abdominal cavity. Typically, a colostomy bag is connected to the stoma site with an adhesive to collect waste materials from the internal body vessel. Although a stoma has no sensory nerve endings and is insensitive to pain, several complications can result at the stoma site where the colostomy bag is secured, such as leaks, skin irritation, infection, etc. As such, the condition of the stoma must be assessed regularly.

Thus, there is a continuing need in the medical arts for an alternative mechanism for collecting fecal matter or waste material from an internal body vessel that overcomes the above disadvantages and can improve the quality of life of patients requiring ostomy.

SUMMARY

One aspect of the disclosure is directed to a stomal diverter device that includes a catheter, a stoma rod, and a bracket. The catheter has a body defining a first tube having an open end, a second tube spaced from the first tube having a closed end, and a drain tube. The first tube is configured to be received within a first opening of a body vessel to receive bodily fluids. The second tube is configured to be received within a second opening of the body vessel. The drain tube has an open end that is configured to extend from an abdomen of a patient and is in fluid communication with the first and second tubes. The stoma rod is configured to be positioned between the first and second tubes and includes structure to releasably attach the stoma rod to the abdomen of the patient. The stoma rod also defines a mating feature. The bracket is supported on the catheter and the stoma rod and defines a locking feature that is configured to engage the mating feature of the stoma rod to secure the catheter between the stoma rod and the bracket to the abdomen of the patient.

In embodiments, the structure of the stoma rod includes a lower surface, an upper surface, and a pair of posts extending from the upper surface, wherein each post defines the mating feature.

In some embodiments, the lower surface of the stoma rod includes an adhesive pad configured to attach the stoma rod to the abdomen of the patient.

In certain embodiments, the structure of the stoma rod includes a plurality of flanges that extend from an outer surface thereof. Each flange defines a hole therethrough and each hole is configured to receive a fastener to secure the stoma rod to the abdomen of the patient.

In embodiments, the bracket includes an upper surface, a lower surface, and a central circular portion defining an opening. The opening is configured to receive the drain tube of the catheter. In embodiments, a pair of legs extends from the lower surface and each leg defines the locking feature.

In some embodiments, the locking feature of the bracket includes at least one protrusion and the mating feature of the stoma rod includes at least one recess.

In certain embodiments, the first tube includes an anchoring device on an outer surface thereof and the anchoring device is configured to secure the first tube to the first opening of the body vessel.

In embodiments, the anchoring device is at least one inflatable balloon that is selectively inflatable from a deflated position to an inflated position and selectively deflatable from the inflated position to the deflated position. The inflatable balloon is configured to anchor the first tube to the first body vessel in the inflated position.

In some embodiments, the catheter includes a port that is in fluid communication with the at least one inflatable balloon. The port is connectable to one of a source of inflation fluid and a source of vacuum.

In certain embodiments, the second tube includes an anchoring device on an outer surface thereof. The anchoring device is configured to secure the second tube to the second opening of the body vessel.

In embodiments, the anchoring device includes a plurality of ribs.

In some embodiments, the stomal diverter device includes an inflatable balloon that is disposed on an inner surface of the first tube, wherein the inflatable balloon is inflatable from a deflated position to an inflated position and deflatable from the inflated position to the deflated position. The inflatable balloon is configured to obstruct the flow of digestive waste through the first tube in the inflated position.

In certain embodiments, the catheter includes a port that is in fluid communication with the inflatable balloon and is connectable to one of a source of inflation fluid or a source of vacuum.

In embodiments, the stomal diverter device includes a cap that is selectively attachable to the open end of the drain tube and is configured to obstruct the flow of bodily fluids through the open end of the drain tube.

Another aspect of the present disclosure is directed to a surgical method that includes: making an abdominal incision into an abdomen of a patient to provide access to an abdominal cavity of the patient; pulling a loop of a body vessel out of the abdominal cavity through the abdominal incision; positioning a stoma rod across the abdominal incision between the loop of the body vessel and the abdomen of the patient to prevent the loop of the body vessel from receding back into the abdominal cavity of the patient; making a first incision into the body vessel to define a first opening within the body vessel; making a second incision into the body vessel to define a second opening within the body vessel; inserting a first tube of a catheter into the first opening of the body vessel and a second tube of the catheter into the second opening of the body vessel such that a drain tube that is in fluid communication with the first and second tubes of the catheter extends out of the abdomen of the patient; and positioning a bracket over the catheter and the stoma rod and selectively engaging a locking feature of the bracket with a mating feature of the stoma rod to secure the first and second tubes within the first and second openings of the body vessel.

In embodiments, the method further comprises positioning a central portion of the bracket defining an opening therethrough over the drain tube and advancing the bracket towards the drain tube such that the drain tube is received within the opening.

In some embodiments, the method further comprises attaching a source of inflation fluid to a first port of the catheter and inflating an inflatable balloon disposed an on outer surface of the first tube and in fluid communication with the first port with the source of inflation fluid to secure the first tube to the first opening of the body vessel.

In certain embodiments, the method further comprises attaching a source of inflation fluid to a second port of the catheter and inflating an inflatable balloon disposed on an inner surface of the first tube and in fluid communication with the second port with a source of inflation fluid to obstruct the flow of bodily fluids through the first tube.

In embodiments, the method further comprises attaching a cap to an open end of the drain tube to obstruct the flow of bodily fluids therethrough.

In some embodiments, the method further comprises removing the cap from the open end of the drain tube and attaching a colostomy bag to the open end of the drain tube to permit the flow of bodily fluids into the colostomy bag.

In certain embodiments, the method further comprises removing the second tube from the second opening of the body vessel and inserting at least one of a camera, a surgical instrument, and a drug into the second opening to perform or a diagnostic and/or a therapeutic procedure within the second opening of the body vessel.

BRIEF DESCRIPTION OF THE DRAWINGS

Various embodiments of the presently disclosed stomal diverter device are described herein below with reference to the drawings, wherein.

DETAILED DESCRIPTION OF EMBODIMENTS

Figure 1:
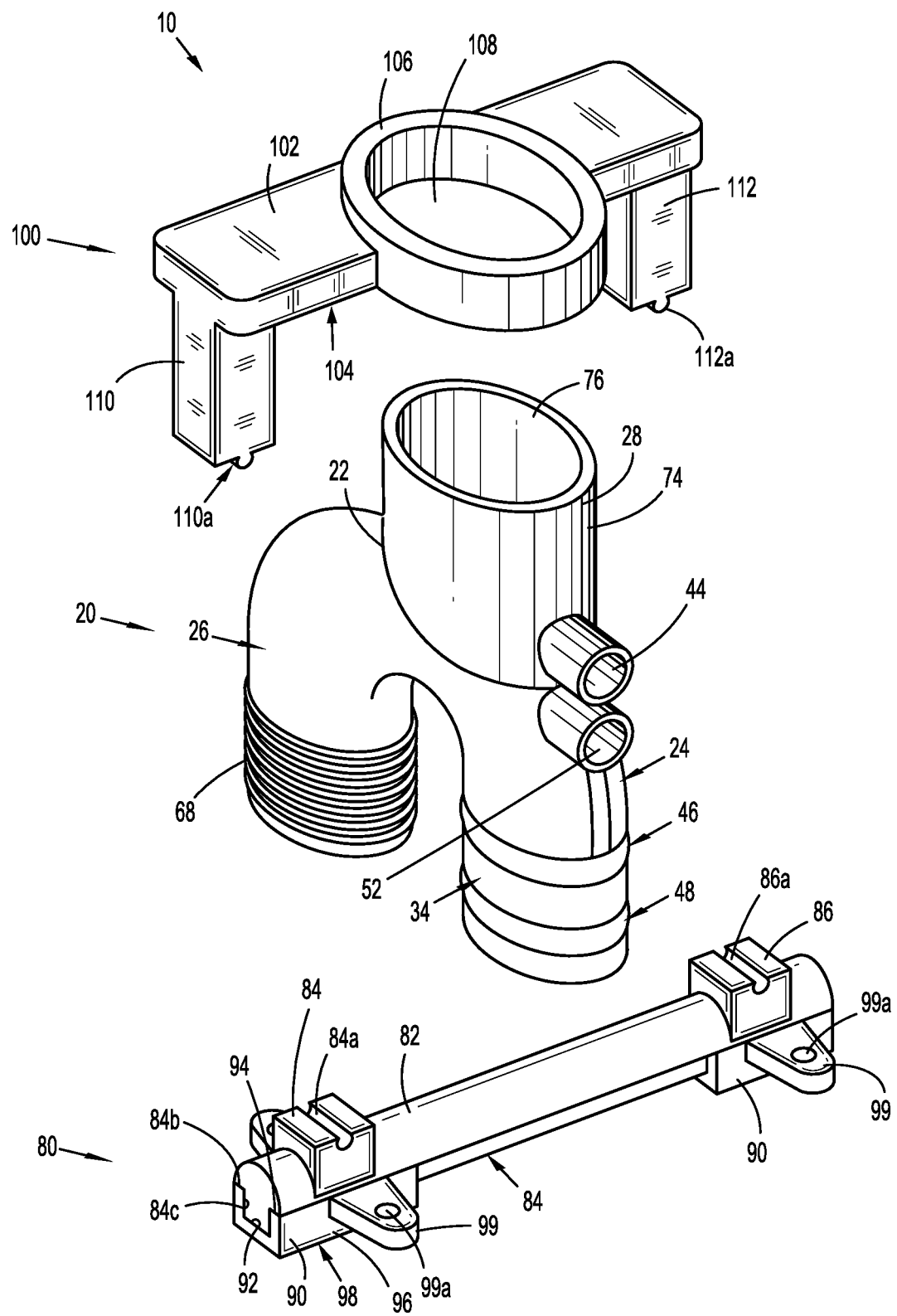
FIG. 1 is a perspective view, with parts separated, of an exemplary embodiment of the presently disclosed stomal diverter device.

The presently disclosed stomal diverter device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The presently disclosed stomal diverter device includes a catheter, a stoma rod, and a bracket. The catheter is configured to attach to first and second openings of a stoma and to permit and/or prohibit the discharge of digestive waste from the stoma. The stoma rod is selectively attachable to the abdomen of a patient and is securable between the abdomen of the patient and the stoma. The bracket is selectively attachable to the catheter and to the stoma rod to secure the catheter to the stoma. The stomal diverter device provides an interface between the stoma and a waste containment device, e.g., a colostomy bag, to prevent complications that are typically associated with colostomy bags attached directly to stoma sites (e.g., leaks, skin irritation, infections, etc.). In addition, the stomal diverter device allows a patient to obstruct the waste material from exiting the stoma when use of a colostomy bag is not desired.

Referring to FIG. 1, the presently disclosed stoma diverter device is shown generally as 10 and includes a catheter 20, a stomal rod 80, and a bracket 100. The catheter 20 includes a body 22 defining a first tube 24, a second tube 26, and a drain tube 28. The catheter 20 of the stomal diverter device 10 is generally configured for attachment to a stoma site "ST."

Figure 5:
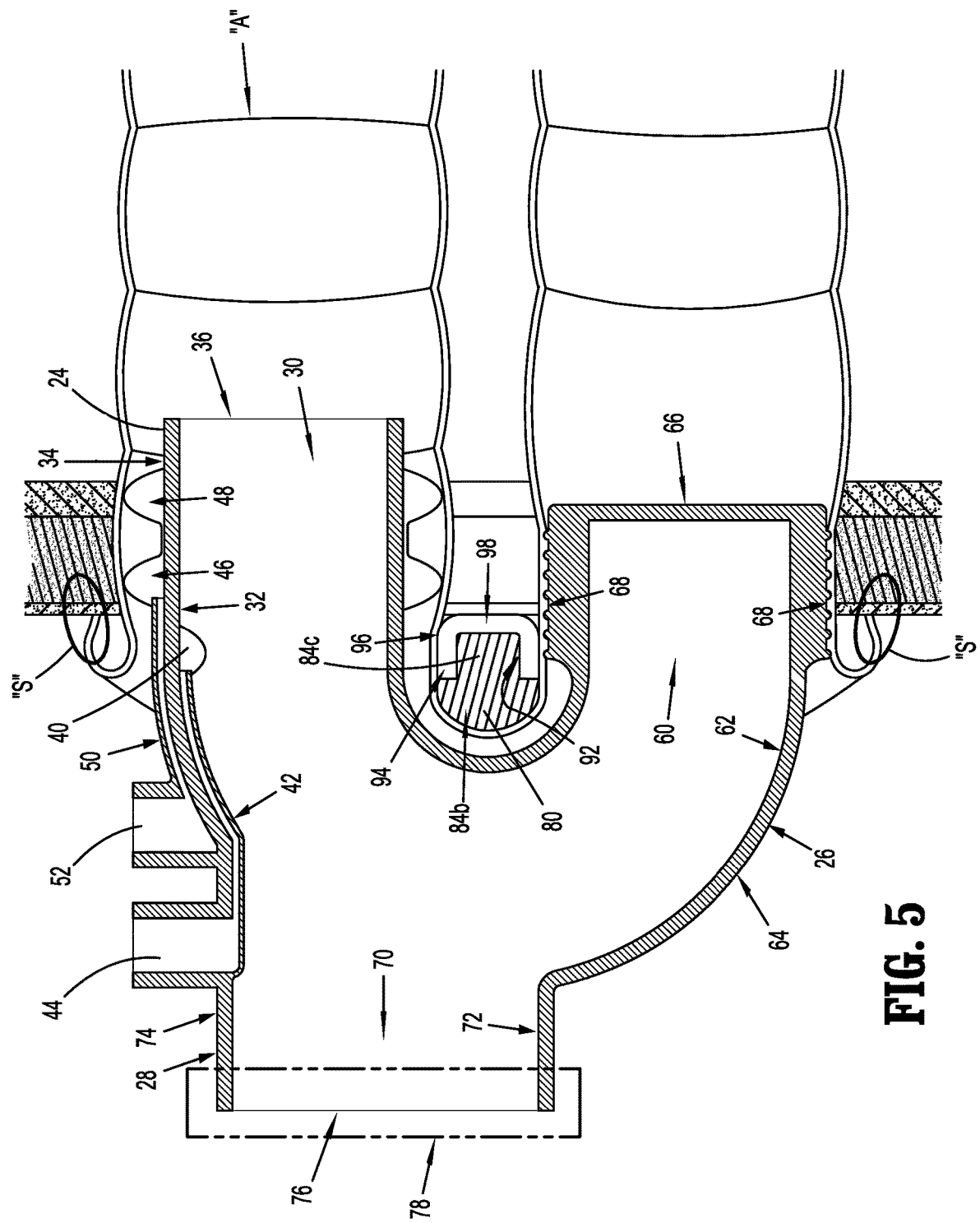
FIG. 5 is a side, cross-sectional view of the stomal diverter device of FIG. 1 taken along section line 5-5 of FIG. 4 with an internal inflatable balloon of a catheter of the stomal diverter device in a deflated position.
Figure 6:
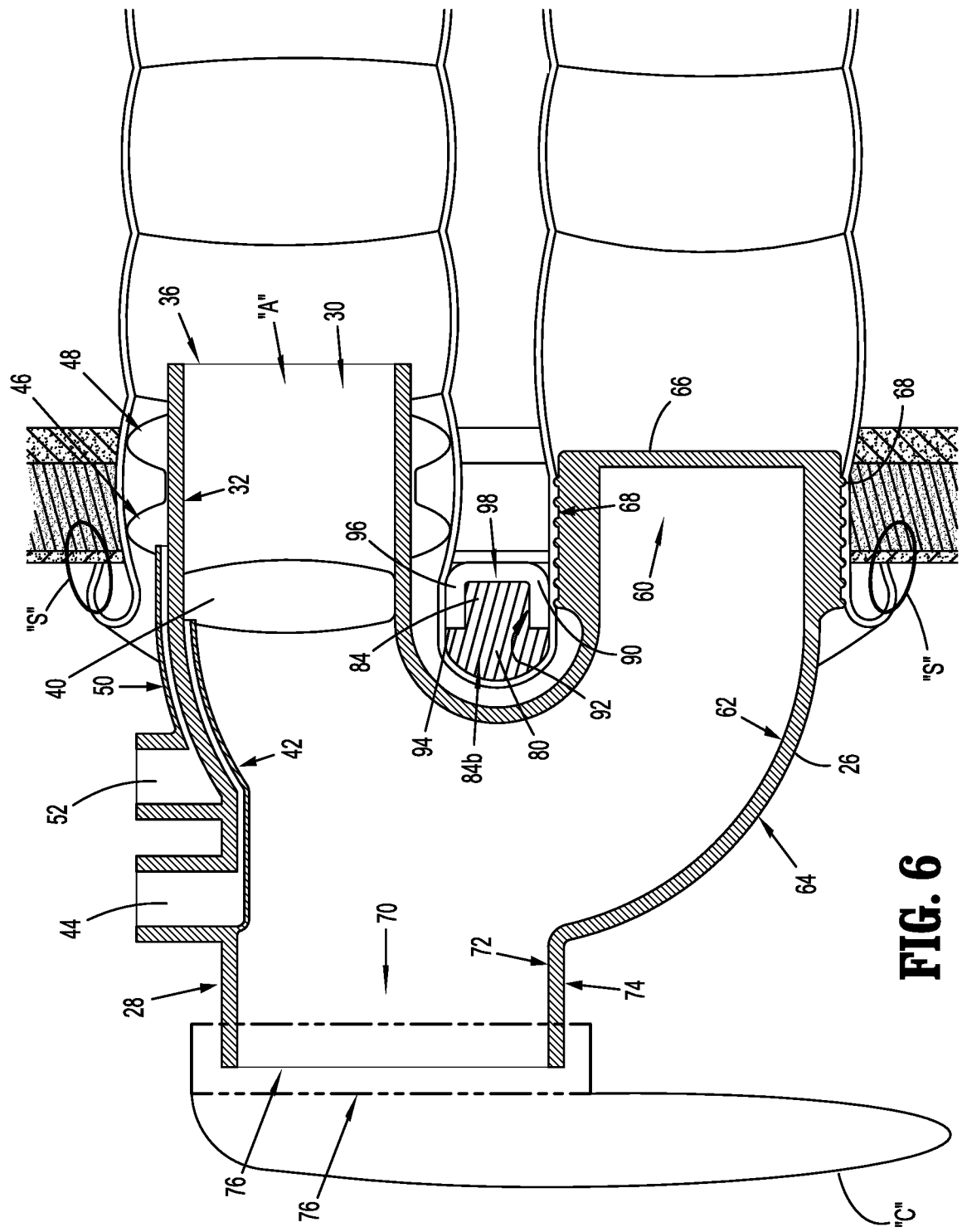
FIG. 6 is a side, cross-sectional view of the stomal diverter device of FIG. 1 taken along section line 6-6 of FIG. 4 depicting the internal inflatable balloon of the catheter of the stomal diverter device in an inflated position and a colostomy bag attached to an open end of a drain tube of the catheter.

Referring also to FIG. 5, the first tube 24 of the catheter 20 inner surface 32 defining a first channel 30, an outer surface 34, and an open end 36. The inner surface 32 of the first tube 24 supports an inflatable balloon 40 that is connected to a fluid line 42, which is in communication with a first port 44. The first port 44 is disposed on the body 22 of catheter 20 and is connectable to an inflation source (not shown) to selectively inflate the inflatable balloon 40 from a deflated position (FIG. 5) to an inflated position (FIG. 6). The first port 44 is also connectable to a vacuum source to deflate the inflatable balloon 40 from the inflated position to the deflated position. The outer surface 34 of the first tube 24 also supports one or more inflatable balloons 46, 48. The inflatable balloons 46, 48 are connected to a fluid line 50, which is in communication with a second port 52. The second port 52 is disposed on the body 22 of the catheter 20 and is connectable to an inflation source to facilitate inflation of the inflatable balloons 46, 48 from a deflated position to an inflated position (FIGS. 5 and 6). The second port 52 is connectable to a vacuum source (not shown) to selectively deflate the inflatable balloons 46, 48 from the inflated position to the deflated position.

The second tube 26 includes an inner surface 62 defining a second channel 60, an outer surface 64, and a closed end 66. The outer surface 64 of the second tube 26 defines a plurality of anchoring elements or ribs 68. The second tube 26 may be oriented transversely relative to the first tube 24 such that the first tube 24 and the second tube 26 define a bifurcated configuration.

The drain tube 28 includes an inner surface 72 defining a discharge channel 70 that is in fluid communication with the first channel 30 of the first tube 24 and the second channel 60 of the second tube 26. The drain tube 28 also includes an outer surface 74 and an open end 76. The open end 76 of the drain tube 28 may be configured to receive a valve or cap 78 (FIG. 5) for obstructing the flow of digestive waste through the open end 76 of the drain tube 28. The cap 78 can be removed to allow for the flow of digestive waste through the open end 76 of the drain tube 28. With the cap 78 removed from the open end 76 of the drain tube 28, a waste containment device, e.g., a colostomy bag "C" (FIG. 6), may be secured to the open end 76 of the drain tube 28, as will be described below.

In embodiments, the outer surface 34 of the first tube 24 may include a plurality of ribs (e.g., similar to the ribs 68 of the second tube 26), clips, or the like, in lieu of, or in addition to the inflatable balloons 46, 48 for securing the first tube 24 to a stoma "ST." Likewise, the outer surface 64 of the second tube 26 may include inflatable balloons in lieu of, or in addition to ribs 68. It should be appreciated that any number of anchoring devices in, or on first tube 24, second tube 26, and drain tube 28 are contemplated.

With continued reference to FIGS. 1 and 5, the stoma rod 80 has an upper surface 82 and a lower surface 84. The upper surface 82 includes a first post 84, and a second post 86. Each of the first and second posts 84, 86 includes a mating feature or recess 84a, 86a. The lower surface 84 of the stoma rod 80 has a flared portion 84b and a reduced width portion 84c. The lower surface 84 of the stoma rod 80 supports one or more adhesive pads 90. In embodiments, each adhesive pad 90 may have a generally C-shaped cross section and include an inner surface 92, an upper surface 94, a side surface 96, and a tissue contacting surface 98. The inner surface 92 of each adhesive pad 90 receives a reduced width portion 84c of stoma rod 80, and the upper surface 94 of each adhesive pad 90 supports a flared portion 84b of the stoma rod 80. The side surfaces 96 of the adhesive pads 90 include one or more fastening ears 99. Each fastening ear 99 defines a hole 99a that is configured to receive a fastener (not shown).

In embodiments, the stoma rod 80 may have any suitable cross-sectional shape such as a semi-circular, circular, square, rectangular, or the like. In some embodiments, the stoma rod 80 may be formed from pliable, semi-rigid, or rigid material, such as a plastic, a polymer, a metal, or the like. In certain embodiments, each adhesive pad 90 may be a flat sheet, sticker, tape, or the like. In embodiments, the adhesive pads 90 may include any type of biocompatible adhesive (e.g., glue). In some embodiments, the lower surface 84 of the stoma rod 80 may optionally include an adhesive coating in lieu of the adhesive pads 90.

With reference to FIG. 1, the bracket 100 includes an upper surface 102 and a lower surface 104. The upper surface includes a circular central portion 106 that defines a circular opening 108. The lower surface 104 of the bracket 100 supports a pair of spaced legs 110, 112. Each of the pair of legs 110, 112 includes a distal portion having a mating feature or protrusion 110a, 112a that is configured to engage with a respective one of the mating features or recesses 84a, 86a of the stoma rod 80. In embodiments, the bracket 100 may be formed from any suitable material, such as plastic, ceramic, metal, composite, or the like.

Figure 2:
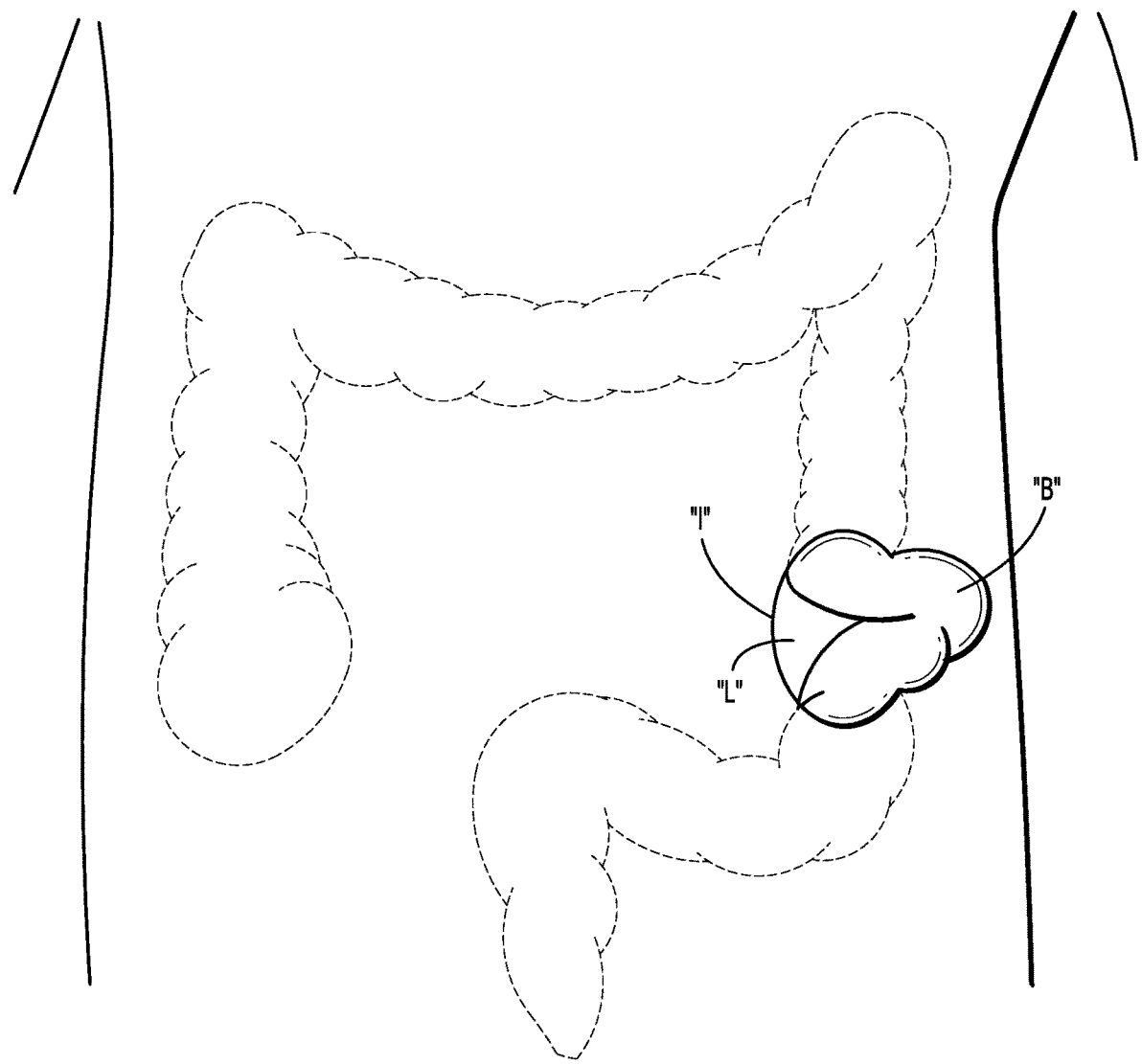
FIG. 2 is a schematic diagram of a surgical site illustrating an initial stage of a method for performing an ostomy procedure.
Figure 3:
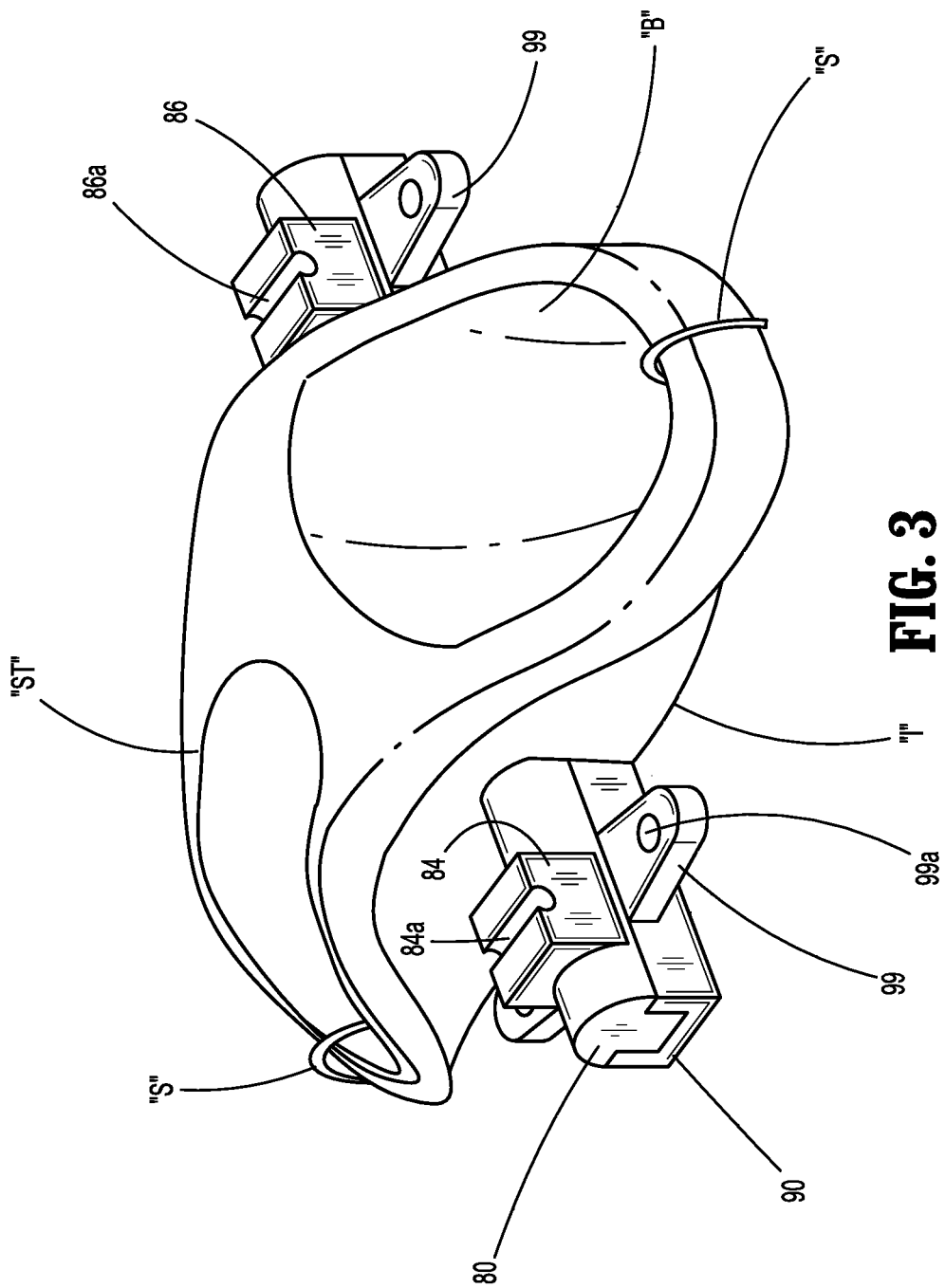
FIG. 3 is a perspective view of a stoma rod of the stomal diverter device of FIG. 1 secured between an abdomen of a patient and a stoma site.

With reference to FIGS. 2 and 3, in use, for example, in a loop ostomy procedure (e.g., a diverting sigmoid loop colostomy, loop ileostomy, etc.), an incision is made into a patient's abdomen at an incision site "I." A portion or loop "L" of the body vessel is pulled outwardly through the incision site "I" such that the loop "L" extends out of the patient's abdomen. In order to prevent the loop "L" from receding through the incision site "I" and back into the abdominal cavity, the stoma rod 80 is positioned centrally between the loop "L" and the patient's abdomen (e.g., at skin level). The tissue contacting surfaces 98 of the adhesive pads 90 of the stoma rod 80 are brought into contact with the patient's abdomen adjacent the incision site "I" to secure the stoma rod 80 to the patient's abdomen. In embodiments, fasteners (not shown) can be driven through holes(s) 99a of the fastening ears 99 of the adhesive pads 90 through the patient's abdomen or skin, to further secure the stoma rod 80 to the patient. With the tissue contacting surface 98 of the adhesive pad 90 of the stoma rod 80 secured to the patient's abdomen and the stoma rod 80 secured between loop "L" and the abdominal wall, the body vessel "B" is prevented from receding back into the abdominal cavity.

Figure 4:
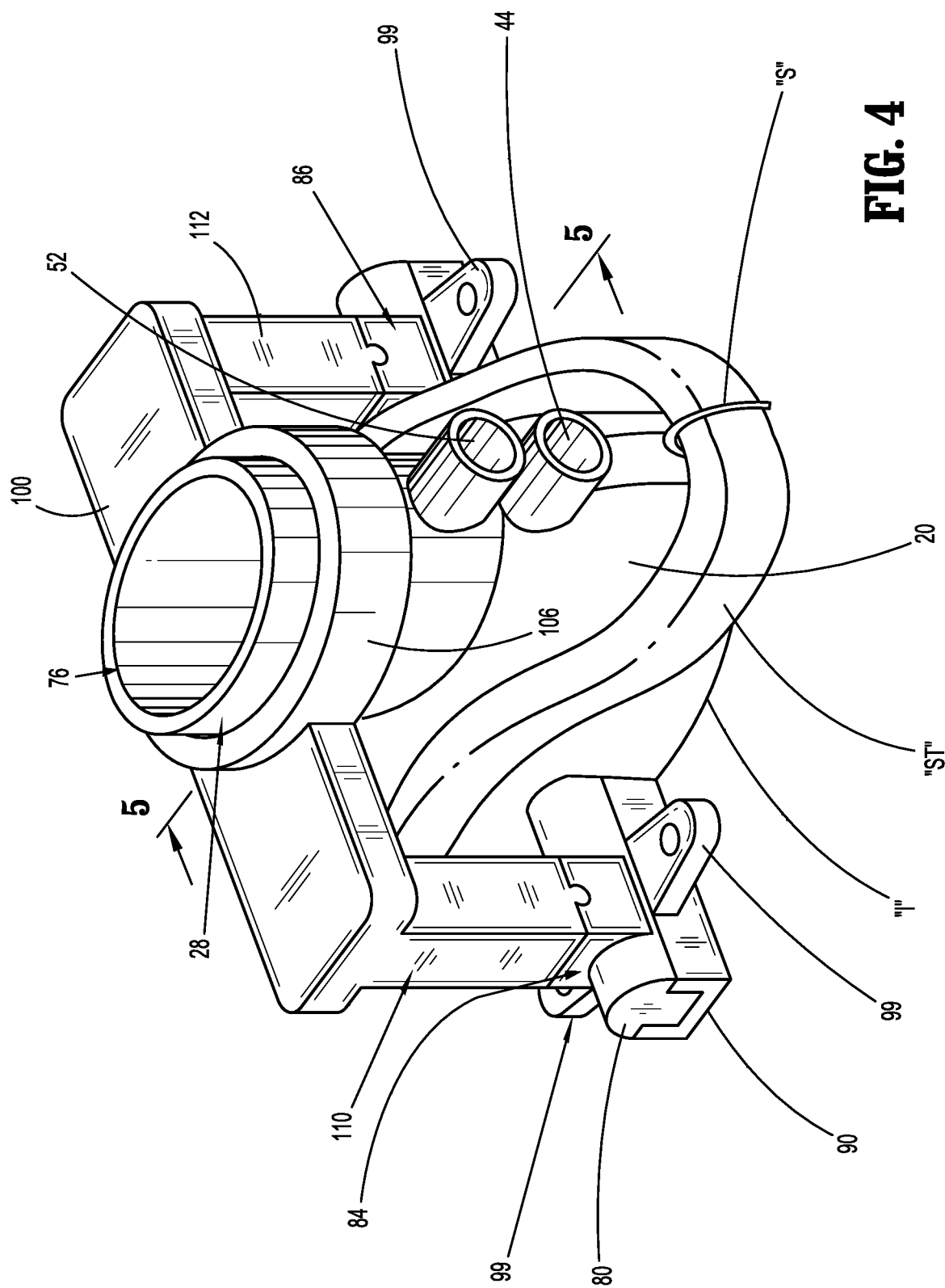
FIG. 4 is a perspective view, with parts assembled, of the stomal diverter device of FIG. 1 secured to the stoma site.

With reference also to FIGS. 5 and 6, a first incision is made into a body vessel "B" to create a first opening therein. In embodiments, the body vessel "B" may include the bowel, e.g., small or large intestine, colon, or rectum. For example, the first opening may be formed in the upstream portion of the large intestine. A second incision is made into the body vessel to create a second opening therein. The second opening may be formed within the body vessel, such as, e.g., the downstream portion of the intestine. The first and second openings define the stoma "ST" (FIGS. 3 and 4). Each of the first and second openings is then affixed or sutured to the abdomen (e.g., at skin level) using one or more sutures "S" (FIGS. 3-6). The catheter 20 is then attached to the stoma "ST." Specifically, the first tube 24 of the catheter 20 is inserted into the first opening of the stoma "ST" and the second tube 26 of the catheter 20 is inserted into the second opening of the stoma "ST." With the catheter 20 attached to the stoma "ST," the drain tube 28 of the catheter 20 extends outwardly from patient's abdomen.

With reference to FIG. 4, the bracket 100 is advanced towards the catheter 20 such that the central circular portion 106 of the bracket 100 aligns with the drain tube 28. Specifically, the bracket 100 is advanced toward the catheter 20, until the outer surface 74 of the drain tube 28 is received within the opening 108 of the bracket 100. The mating features 110a, 112a of the bracket 100 are then engaged with the respective mating features 84a, 86a of the stoma rod 80. With the drain tube 28 received within the opening 108 of the bracket 100, and with the mating features 110a, 112a of the bracket 100 engaged with the mating features 84a, 86a of the stoma rod 80, the catheter 20 is further secured to the stoma "ST" and is prevented from slipping or backing out of the patient.

Referring to FIG. 5, to further secure catheter 20 to the stoma "ST," an inflation source may be connected to the second port 52 to send inflation fluid through the fluid line 50 (FIG. 6) into the inflatable balloons 46, 48. As the inflatable balloons 46, 48 are inflated, the first tube 24 is anchored within the first opening of the stoma "ST." Likewise, the ribs 68 on the outer surface 74 of the second tube 26 serve to anchor or secure the second tube 26 within the second opening of the stoma "ST." In embodiments, other anchoring mechanisms, such as clips, fasteners, mechanical anchors, etc., may be used to secure the catheter 20 within the first and second openings within the "ST."

Referring to FIG. 6, with the catheter 20 secured to the stoma "ST," the stomal diverter device 10, a containment device or colostomy bag "C" may be attached to the outer surface 74 of the drain tube 28. As the patient undergoes normal digestive processes (e.g., excretion), digestive waste flows, in the direction indicated by arrow "A," from the first opening of the stoma "ST" (e.g., the upstream portion of the intestine) through the first channel 30 of the first tube 24, through the discharge channel 70 of the drain tube 28, and into the colostomy bag "C." The second tube 26 separates the second opening of the stoma "ST" from the first opening of the stoma 'ST," e.g., to keep the downstream portion of the intestine clean, and/or to allow for healing of the intestine. As such, no fluid can flow from the second tube 26 of the catheter 20 into the downstream portion of the intestine.

When use of the colostomy bag "C" is not desired, the patient or the clinician can remove the colostomy bag "C" and place the cap 78 (FIG. 5) on the open end 76 of the drain tube 28. As such, digestive waste exiting the first opening of the stoma "ST" is prevented from exiting from the open end 76 of the drain tube 28 and out of the patient. To prevent digestive waste from further entering the catheter 20, the patient or the clinician can connect an inflation source to the first port 44 to send inflation fluid from the inflation source through the fluid line 42 and into the inflatable balloon 40 to selectively inflate the inflatable balloon 40. With the inflatable balloon 40 in the fully inflated position, the inflatable balloon 40 obstructs digestive waste from flowing through the first opening of the stoma "ST" and into drain tube 28 or the second tube 26.

The patient or clinician can selectively deflate the inflatable balloon 40 by connecting the first port 44 to a vacuum source (not shown). With the inflatable balloon 40 deflated, digestive wastes can flow from the first opening of the stoma "ST" into the first channel 30 of the first tube 24, and through the discharge channel 70 out of the open end 76 of the drain tube 28 (e.g., into a colostomy bag or other containment device, once cap 78 is removed).

If desired, the patient or the clinician can remove (e.g., by rotating, pulling, etc.) the second tube 26 from the second opening of the stoma "ST," while leaving the first tube 24 secured to the first opening of the stoma "ST." With the second opening of the stoma "ST" exposed, a clinician can insert one or more cameras, surgical instruments, drugs, therapies, etc., in the second opening of the stoma "ST" to perform a diagnostic (e.g., colonoscopy) or therapeutic procedure on the body vessel. Likewise, a clinician may leave the second tube 26 in place in the second opening of the stoma "ST" and remove the first tube 24 from the first opening of the stoma "ST," and perform diagnostic and/or therapeutic procedures therein.

When complete removal of the stomal diverter catheter 10 is desired, the first and second tubes 24, 26 are removed from the respective first and second openings of the stoma "ST." The clinician or the patient can then gently detach the adhesive pad 90 of the stoma rod 80 from the patient's abdomen and remove the stoma rod 80 from the loop "L" of the body vessel. The clinician and/or the patient can then examine the stoma "ST."

If needed or desired, the stomal diverter device 10 can then be re-attached to the stoma "ST" using the procedures described above. In order to prevent any possible skin irritation at the stoma "ST," the adhesive pads 90 of the stoma rod 80 may be positioned at a different location than the original site of attachment to the patient's abdomen. For example, the stoma rod 80 may be rotated (e.g., from 45 degrees, 90 degrees, 120 degrees, etc.) relative to the original site of attachment to ensure that the adhesive pads 90 of the stoma rod 80 contact the patient's abdomen at a different location the original site of attachment. It should be appreciated that a clinician may install or remove stomal diverter device 10 from a patient, as necessary, e.g., in an outpatient setting. Additionally, a patient can perform installation or removal of stomal diverter device 10, as necessary (e.g., at home).

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A stomal diverter device, comprising:
a catheter including a body defining a first tube having an open end and a second tube spaced from the first tube and having a closed end, the first tube configured to be received within a first opening of a body vessel to receive bodily fluids, the second tube configured to be received within a second opening of the body vessel, and a drain tube defining an open end, the drain tube in fluid communication with the first and second tubes and configured to extend from an abdomen of a patient;
a stoma rod configured to be positioned between the first and second tubes, the stoma rod releasably attachable to the abdomen of the patient and having a mating feature; and
a bracket releasably supported on the catheter and the stoma rod, the bracket having a central circular portion defining an opening that receives the drain tube and a locking feature configured to engage the mating feature of the stoma rod to releasably secure the catheter between the stoma rod and the bracket to the abdomen of the patient.

2. The stomal diverter device according to claim 1, wherein the stoma rod includes a lower surface, an upper surface, and a pair of posts extending from the upper surface, each post defining the mating feature.

3. The stomal diverter device according to claim 2, wherein the lower surface of the stoma rod includes an adhesive pad configured to attach the stoma rod to the abdomen of the patient.

4. The stomal diverter device according to claim 3, wherein the stoma rod includes a plurality of flanges extending from an outer surface thereof, each flange defining a hole therethrough, each hole configured to receive a fastener to secure the stoma rod to the abdomen of the patient.

5. The stomal diverter device according to claim 1, wherein the bracket includes:
   an upper surface, a lower surface, and the central circular portion; and
   a pair of legs extending from the lower surface, each leg defining the locking feature.

6. The stomal diverter device according to claim 1, wherein the locking feature of the bracket includes at least one protrusion and the mating feature of the stoma rod includes at least one recess.

7. The stomal diverter device according to claim 1, wherein the first tube includes an anchoring device on an outer surface thereof, the anchoring device configured to secure the first tube to the first opening of the body vessel.

8. The stomal diverter device according to claim 7, wherein the anchoring device is at least one inflatable balloon that is selectively inflatable from a deflated position to an inflated position and selectively deflatable from the inflated position to the deflated position, wherein the inflatable balloon is configured to anchor the first tube to the first body vessel in the inflated position.

9. The stomal diverter device according to claim 8, wherein the catheter includes a port that is in fluid communication with the at least one inflatable balloon, the port connectable to one of a source of inflation fluid or a source of vacuum.

10. The stomal diverter device according to claim 1, wherein the second tube includes an anchoring device on an outer surface thereof, the anchoring device configured to secure the second tube to the second opening of the body vessel.

11. The stomal diverter device according to claim 10, wherein the anchoring device includes a plurality of ribs.

12. The stomal diverter device according to claim 1, further comprising an inflatable balloon disposed on an inner surface of the first tube, the inflatable balloon inflatable from a deflated position to an inflated position and deflatable from the inflated position to the deflated position, wherein the inflatable balloon is configured to obstruct the flow of digestive waste through the first tube in the inflated position.

13. The stomal diverter device according to claim 12, wherein the catheter includes a port that is in fluid communication with the inflatable balloon, the port connectable to one of a source of inflation fluid and a source of vacuum.

14. The stomal diverter device according to claim 1, further comprising a cap selectively attachable to the open end of the drain tube, the cap configured to obstruct the flow of bodily fluids through the open end of the drain tube.

15. A stomal diverter device, comprising:
   a catheter including a body including a first tube having an open end and a second tube spaced from the first tube having a closed end, the first tube configured to be received within a first opening of a body vessel to receive bodily fluids, the second tube configured to be received within a second opening of the body vessel, and a drain tube in fluid communication with the first and second tubes;
   a stoma rod positioned between the first and second tubes, the stoma rod releasably attachable to the abdomen of the patient; and
   a bracket releasably supported on the catheter and the stoma rod, the bracket having a central portion defining an opening that receives the drain tube, the bracket adapted to releasably secure the catheter between the stoma rod and the bracket.

16. The stomal diverter device of claim 15, wherein the stoma rod includes a lower surface, an upper surface, and a pair of posts extending from the upper surface, the lower surface of the stoma rod supporting an adhesive pad to facilitate attachment of the stoma rod to the abdomen of the patient.

17. The stomal diverter device of claim 16, wherein each of the posts define a mating feature, and the bracket includes an upper surface, a lower surface, and a pair of legs extending from the lower surface, each leg of the pair of legs defining a locking feature that is configured to be coupled to a respective one of the mating features of the stoma rod.

\* \* \* \* \*